United States Patent [19]

Burke

[11] Patent Number: 5,077,425
[45] Date of Patent: Dec. 31, 1991

[54] NITRILE-ACCELERATED HYDROCARBOXYLATION
[75] Inventor: Patrick M. Burke, Wilmington, Del.
[73] Assignee: E. I. du Pont de Nemours and Company, Wilmington, Del.
[21] Appl. No.: 502,756
[22] Filed: Apr. 2, 1990
[51] Int. Cl.$^5$ ..................... C07C 253/30; C07C 51/14
[52] U.S. Cl. ................................. 558/353; 560/190; 560/204; 562/522
[58] Field of Search .................. 562/522; 558/353; 560/190, 204

[56] References Cited

U.S. PATENT DOCUMENTS 3,579,552  5/1971  Craddock et al. ............. 549/39 X
4,788,334 11/1988  Burke ......................... 560/204 X Primary Examiner—Joseph Paul Brust

[57] ABSTRACT

A process for the hydrocarboxylation of alkenes and non-conjugated olefinically unsaturated nitriles and esters using a rhodium catalyst, a bromide or iodide promoter, and a nitrile accelerator.

3 Claims, No Drawings

NITRILE-ACCELERATED HYDROCARBOXYLATION

FIELD OF THE INVENTION

This invention relates to the nitrile-accelerated hydrocarboxylation of olefinically unsaturated compounds.

BACKGROUND OF THE INVENTION

Craddock et al., U.S. Pat. No. 3,579,552 discloses the hydrocarboxylation of olefinically unsaturated compounds using rhodium catalysts and iodide promoters in which the reactant is dissolved in a compatible solvent. Acrylonitrile is listed as a suitable feedstock.

Burke, U.S. Pat. No. 4,788,334 discloses the hydrocarboxylation of olefinically unsaturated alkenes or esters using a rhodium catalyst, an iodide promoter, a solvent selected from the class consisting of methylene chloride, 1,2-dichloroethane, and $C_6$ to $C_9$ aromatic solvents, and an accelerator which is an acid having a pKa in the range of 4.2 to 5.2.

SUMMARY OF THE INVENTION

The present invention is a process for the nitrile-accelerated hydrocarboxylation of an olefinically unsaturated compound selected from the group consisting of alkenes and non-conjugated olefinically unsaturated nitriles and esters to form the corresponding carboxylic acid, which comprises reacting in a solvent selected from the group consisting of methylene chloride, 1,2-dichloroethane, and aromatic solvents having 6 to 9 carbon atoms: said compound, carbon monoxide, and water with a rhodium catalyst, a promoter selected from the class consisting of bromide and iodide, and a nitrile accelerator selected from the group consisting of $C_2$ to $C_{10}$ aliphatic nitriles and $C_6$ to $C_{10}$ aromatic nitriles at a temperature of about 100° C. to about 250° C. and at a carbon monoxide partial pressure in the range of about 200 to about 3,000 psig, wherein the concentration of rhodium is in the range of 0.005% to about 0.50% by weight of the total weight of the reaction mixture, the molar ratio of nitrile to rhodium is between about 10 and about 700, and the molar ratio of promoter to rhodium is between 1:1 and 20:1.

DETAILED DESCRIPTION OF THE INVENTION

Although it had previously been shown that aliphatic and aromatic acids accelerate the rhodium-catalyzed hydrocarboxylation of selected olefins, accelerator effects had not been demonstrated, or expected, for other classes of compounds. It has now been found that aliphatic and aromatic nitriles can also greatly accelerate the rhodium-catalyzed hydrocarboxylation of selected olefins and substituted olefins. The nitrile accelerator may be added separately, or may be part of the olefinic substrate, provided that when the nitrile is part of the olefinic compound, it is separated from the olefinic double bond by at least one carbon.

Suitable olefinically unsaturated compounds useful in the process of this invention include alkenes and substituted alkenes having the formula:

$$CHR=CR^1(CHR^2)_nX$$

wherein i) X is $-C(O)OR^3$;
R, $R^1$ and $R^3$ are independently selected from the group consisting of $-H$, $-CH_3$, and $-C_2H_5$;
$R^2$ is $-H$ or $-CH_3$; and
n = 1–5; or ii) X is $-CH=CH_2$;
R and $R^1$ are independently selected from the group consisting of $-H$, $-CH_3$, and $C_2H_5$;
$R^2$ is $-H$ or $-CH_3$; and
n is 0–6; or iii) X is selected from the group consisting of $-H$, and $-CN$;
R and $R^1$ are independently selected from the group consisting of $-H$, $-CH_3$, and $-C_2H_5$;
$R^2$ is $-H$ or $-CH_3$; and
n = 1–13

Preferred compounds include, but are not limited to, methyl-3-pentenoate, methyl-4-pentenoate, 1,3-butadiene, 1,4-pentadiene, 1,5-hexadiene, 1-butene, 1-pentene, 1-hexene, 1-heptene, and 4-pentenenitrile. These compounds are commercially available, or can be made by known methods.

Suitable nitrile accelerators for the process of this invention are $C_2$ to $C_{10}$ aliphatic or $C_6$ to $C_{10}$ aromatic nitriles which are added separately to the reaction mixture, or are compounds, $CH_2=CH(CHR^2)_nCN$ (n = 1–13; $R^2=H$, or $CH_3$), in which the nitrile group is incorporated into the olefinically unsaturated compound. In aliphatic nitriles, the nitrile group may be attached to a primary or secondary carbon. Preferred accelerators include, but are not limited to, acetonitrile, benzonitrile and propionitrile.

The molar ratio of accelerator to rhodium appears to influence the accelerator effect observed, such that the preferred range is about 10 to about 700, most preferably about 80 to about 300.

Suitable solvents for the reaction include methylene chloride, 1,2-dichloroethane and $C_6$ to $C_9$ aromatic solvents, including benzene, toluene, ethyl benzene, and xylenes, or mixtures thereof. The amount of solvent employed is typically between about 40% to about 99%, preferably 60% to 99%, and more preferably between about 85% to about 95% of the weight of the reaction mixture.

The rhodium catalyst can be provided from any source or by any material which will produce rhodium ions under hydrocarboxylation conditions. Among the materials which can be employed as the source of the rhodium catalyst are rhodium metal, rhodium salts, rhodium oxides, rhodium carbonyl compounds, organorhodium compounds, coordination compounds of rhodium, and mixtures thereof. Specific examples of such materials include, but are not limited to, rhodium-(III) chloride and its hydrates, $RhI_3$, $Rh(CO)_2I_3$, $Rh(CO)I_3$, rhodium(III) nitrate trihydrate, $Rh_4(CO)_{12}$, $Rh_6(CO)_{16}$, $Rh(acac)_3$, $Rh(CO)_2(acac)$, $Rh(C_2H_4)_2(acac)$, $[Rh(C_2H_4)_2Cl]_2$, $[Rh(CO)_2Cl]_2$, $Rh(COD)(acac)$, $[Rh(COD)Cl]_2$, $RhCl(CO)(PPh_3)_2$, $Rh_2[O_2C(CH_2)_6CH_3]_4$ and $Rh_2(acetate)_4$, where acac is acetylacetonate and COD is 1,5-cyclooctadiene. Supported rhodium compounds, e.g., Rh/C and Rh/alumina, can also be used as a source of the rhodium catalyst. Rhodium compounds containing bidentate phosphine or nitrogen ligands should be avoided. Preferred sources of the rhodium catalyst include rhodium(I) compounds such as $[Rh(CO)_2Cl]_2$, $[Rh(COD)Cl]_2$, and $Rh(COD)(acac)$, and rhodium iodide compounds such as $RhI_3$ and $Rh(CO)_2I_3$. The bromine analogs of the chlorine- or iodine-containing rhodium compounds listed above are also suitable sources of the rhodium catalyst.

Suitable concentrations of rhodium in the reaction medium are in the range of 0.005–0.50% by weight of rhodium metal based on the weight of the reaction medium. Preferably, the concentration of rhodium is in the range of 0.01–0.20 wt %, more preferably 0.02–0.10 wt %.

The rhodium catalyst, which can be preformed or formed in situ, must be promoted by bromide or iodide, preferably iodide, to achieve a satisfactory reaction rate. The promoter can be provided by HX (X=I, Br), $X_2$, MX (M=alkali metals), $M'X_2$ (M'=alkaline earth metals), transition metal bromides, transition metal iodides, including certain rhodium halides, or any organic halide which will provide bromide or iodide. Suitable sources of bromide or iodide include bromine, iodine, HI, HBr, organic bromide compounds, organic iodide compounds, and mixtures thereof. Preferred sources of iodide and bromide include HI, HBr, acetyl bromide, acetyl iodide, lower alkyl bromides ($C_1$–$C_{10}$) and lower alkyl iodides ($C_1$–$C_{10}$), such as methyl bromide, bromoethane, 1-bromobutane, 1,4-dibromobutane, 2-bromopropane, 1-bromopropane, bromoheptane, methyl iodide, iodoethane, 1-iodobutane, 1,4-di-iodobutane, 2-iodopropane, 1-iodopropane and iodoheptane. The promoter and rhodium can also be present in the same compound, e.g., as in $RhI_3$. The most preferred sources of promoters are HI, HBr and methyl iodide.

The molar ratio of promoter to Rh must be between about 1:1 and 20:1, preferably between about 1:1 and 15:1, more preferably between about 1:1 and 8:1, and most preferably between about 2:1 and 6:1.

The process of this invention can be run either as a batch or as a continuous process.

The temperature of the reaction is in the range of about 100° C. to about 250° C.; 100° C.–225° C. is preferred and 130° C.–180° C. is most preferred.

Suitable total pressures are in the range of 300–3,000 psig, with 400–1,200 psig being preferred. The partial pressure of carbon monoxide is usually maintained in the range of 200–3,000 psig, preferably 200–1,000 psig.

The source of carbon monoxide (CO) is not critical, and commercially available grades of carbon monoxide are satisfactory. The carbon monoxide can contain inert impurities such as carbon dioxide, methane, nitrogen, noble gases, and paraffinic hydrocarbons having from 1 to 4 carbon atoms. The hydrocarboxylation of the olefinically unsaturated compound requires at least a 1:1 molar ratio of CO:compound, but a large excess is usually used.

Water, which is necessary for the hydrocarboxylation of the olefinically unsaturated compound, can be obtained from water added to the reaction mixture or from water formed under the reaction conditions (for example from the formation of esters or anhydrides). However, the water should not be present in large excess. Preferably, water is present in an amount of less than 15%, more preferably less than 10%, and most preferably less than 5%, based on the weight of the reaction mixture. (The weight of the reaction mixture includes the weight of the solvent(s), catalyst(s), promoter(s), accelerator(s) and reactants.) The water may be present in the solution at the beginning of the reaction or it may be added continuously as consumed by the reaction to avoid undesirably high concentrations.

The following examples are presented to illustrate, but not to restrict the present invention. Parts and percentages are by weight and temperatures are in degrees Celsius unless otherwise noted.

EXAMPLES

Example 1

1-Hexene hydrocarboxylation using acetonitrile as accelerator

A 300 mL Hastelloy-C mechanically stirred reactor was flushed with nitrogen and then with high purity carbon monoxide. The reactor was then charged with 150 mL of a methylene chloride solution containing 1-hexene (12.6 g, 150 mmoles), acetonitrile (6.15 g, 150 mmoles), methanol (0.48 g, 15 mmoles), methyl iodide (2.13 g, 15 mmoles), and o-dichlorobenzene (5.0 g, internal standard for gas chromatographic (GC) analysis). The reactor was pressured with CO to 150 psi and then heated to 170° C. The hydrocarboxylation reaction was initiated by injecting, from a 15 mL cylinder connected to the reactor, a solution containing $RhCl_3.3H_2O$ (0.4 g, 1.5 mg-atom of Rh) in 3 mL of water. The reactor pressure was then adjusted to 400 psi with CO. The pressure was maintained at 400 psi by automatically feeding CO to the reactor from a CO reservoir at about 1,200 psi by means of a regulator valve. The uptake of CO, and hence the carbonylation rate, was monitored by measuring the pressure drop in the reservoir by means of a pressure transducer. The pressure drop was related to moles of CO uptake by means of a previous calibration.

Uptake of CO was essentially complete after 2 h. The reaction was terminated by cooling to 20° C. after 5 h and slowly venting the CO. From the pressure drop (84 psi), it was calculated that a total of 105 mmoles of CO per 100 mmoles of 1-hexene was consumed. The rate was first order in 1-hexene to >80% conversion, with a rate constant of $20.5 \times 10^{-3}$ min$^{-1}$.

The product solution was discharged from the reactor and the reactor was washed with 200 mL methanol at 100° C. under pressure and then with 150 mL methanol at ambient temperature. The product and wash solutions were combined and esterified with methanol using a p-toluenesulfonic acid catalyst to convert the carboxylic acid products to the corresponding methyl esters. These methyl esters were analyzed by capillary gas chromatography.

The GC analysis showed 43.1% n-heptanoic acid, 15.1% 2-methyl hexanoic acid, and 1.5% 2-ethylpentanoic acid, based on the amount of 1-hexene added. The selectivity to the linear acid was thus 72.2%. Residual hexenes were not analyzed.

Comparative Example A

1-Hexene hydrocarboxylation in the absence of accelerator

The procedure described in Example 1 was repeated, except that the acetonitrile accelerator was omitted. Uptake of CO was only 16 psi after 5 h. The first order rate constant was $0.85 \times 10^{-3}$ min$^{-1}$.

The reaction was stopped by cooling to room temperature after 5 h. Conversion of the products to the corresponding methyl esters, followed by GC analysis, showed only 13.5% n-heptanoic acid and 3.9% 2-methylhexanoic acid (77.5% linearity).

Thus, the addition of 4% acetonitrile (1 mole per mole 1-hexene) increased the rate by a factor of 24 (=20.5/0.85).

Example 2

1-Hexene hydrocarboxylation at a higher acetonitrile concentration

The procedure described in Example 1 was repeated except that the amount of acetonitrile was increased to 12.3 g (2 moles per mole 1-hexene). Uptake of CO was only 25 psi after 60 min, and 31 psi after 3 h. The product composition was 27.1% heptanoic acid, 9.5% 2-methylhexanoic acid and 0.8% 2-ethylpentanoic acid (analyzed by GC as the methyl esters). Linearity was 72.4%. The initial (first 60 min) first order rate constant was $3.4 \times 10^{-3}$ min$^{-1}$.

Example 3

4-Pentenenitrile hydrocarboxylation

The procedure described in Example 1 was repeated except that the methanol and acetonitrile were omitted and 4-pentenenitrile (12.1 g, 149 mmoles) was substituted for the 1-hexene. Uptake of CO was rapid and essentially complete (62 psi, corresponding to about 77% conversion) in about 75 min. The initial first order rate constant for the reaction, was $28.1 \times 10^{-3}$ min$^{-1}$, i.e., 33 times faster than 1-hexene.

GC analysis of the product as the free acids showed the following results (moles per 100 moles 4-pentenenitrile charged):

| | |
|---|---|
| 4-Pentenenitrile | 15.1 |
| 3-Pentenenitrile | 6.6 |
| 2-Pentenenitrile | 4.8 |
| 2-Methyl-4-cyanobutyric acid | 7.6 |
| 5-Cyanovaleric Acid | 43.4 |

The linear selectivity was 85.1%.

Example 4

3-Pentenenitrile hydrocarboxylation

The procedure described in Example 3 was repeated, except that the 4-pentenenitrile was replaced with an equal amount of 3-pentenenitrile. The uptake of CO was only 24 psi after 24 h. Analysis of the product showed the following results (moles per 100 moles 3-pentenenitrile charged):

| | |
|---|---|
| 3-Pentenenitrile | 79.4 |
| 2-Methyl-4-Cyanobutyric acid | 2.2 |
| 5-Cyanovaleric acid | 11.0 |

The high linearity of the product (83.3%) suggests that 3-pentenenitrile is hydrocarboxylated only after it is isomerized to 4-pentenenitrile under the reaction conditions (a slow process).

Example 5

1,3-Butadiene hydrocarboxylation using acetonitrile accelerator

A 300 mL Hastelloy-C mechanically stirred autoclave was flushed with nitrogen and then with high purity carbon monoxide. This was then charged with 150 mL of a methylene chloride solution containing [Rh(1,5-cyclooctadiene)Cl]$_2$ (0.37 g, 1.5 mmole), acetonitrile (12.3 g, 300 mmole), 2,6-di-t-butyl-4-methylphenol (0.01 g, polymerization inhibitor), o-dichlorobenzene (5.0 g, internal GC standard). The autoclave was closed and 1,3-butadiene was injected with CO pressure from a charge cyclinder containing butadiene (8.1 g, 150 mmole). The autoclave was pressured with CO to 400 psi and then heated to 140° C. The reaction was initiated by injecting into the autoclave a solution make by dissolving 57% aq. HI (1 g, 4.5 mmole HI) in water (2.7 g, 172.5 mmole). The autoclave pressure was then immediately adjusted to 700 psi. The pressure was maintained constant at 700 psi by feeding CO from a reservoir at an initial pressure of 1,180 psi. Carbonylation rate was measured by monitoring the reservoir pressure drop.

The reaction was allowed to run for a total of 98 min, and then cooled to 20° C. The excess CO was vented through a control valve and the product was discharged. The autoclave was washed first with 200 mL methanol at 100° C. under autogenous pressure and then with 150 mL methanol at room temperature.

The product and washes from the autoclave were combined, filtered and the filtrate was diluted to 500 mL with methanol. A sample of this solution was esterified by heating it in a sealed vial at 90° C. for 14 h with excess methanol and p-toluenesulfonic acid esterification catalyst. The resulting solution was determined to have the following composition by capillary gas chromatography of the methyl esters (moles per 100 moles of butadiene in the charging cylinder):

| | |
|---|---|
| Recovered butadiene* | 10.8 |
| Mixed butenes* | 8.5 |
| t-3-Pentenoic acid | 49.6 |
| c-3-Pentenoic acid | 20.8 |
| Valeric acid | 0.9 |
| 2-Methylglutaric acid | 3.2 |
| Ethylsuccinic acid | 2.2 |

*Based on GC analysis of the reactor vapor phase, in which the butadiene concentration decreased from 4.74% (time 0) to a value of 0.51% after 2 h (89% conversion).

No other products were detected in significant amounts and no tars were formed.

Based on the rate of the reservoir pressure drop, the first order rate constant for the carbonylation reaction was $19.4 \times 10^{-3}$ min$^{-1}$.

Examples 6 to 9

Effect of acetonitrile concentration on the rate of butadiene (BD) hydrocarboxylation The procedure in Example 5 was repeated, except that the ratio of acetonitrile-to-rhodium was varied from 0 to 1,600. The following results were obtained:

| Ex. | CH$_3$CN/Rh | Time (min) | Conversion (%) | 3PA* | Rate Constant, $k \times 10^{-3}$ min$^{-1}$ |
|---|---|---|---|---|---|
| 6 | 0 | 150 | 79.2 | 78.2 | 12.6 |
| 7 | 200 | 115 | 98.5 | 76.4 | 27.9 |
| 5 | 400 | 98 | 89.2 | 70.7 | 19.4 |
| 8 | 800 | 150 | 84 | 56.0 | 12.2 |
| 9 | 1600 | 180 | Not Determined | 39.4 | 3.7 |

*Moles per 100 moles of BD charged

Example 10

Hydrocarboxylation of 1-hexene using benzonitrile accelerator

The procedure described in Example 1 was repeated, except that the acetonitrile was replaced with an equimolar amount of benzonitrile (15.5 g, 150 mmole). Uptake of CO was about 77 psi after 90 min. The product composition was 56.5% heptanoic acid, 20.6% 2-methylhexanoic acid, and 4.6% 2-ethylpentanoic acid (analyzed by GC as the corresponding methyl esters). The linearity was 69.1%. The initial (first 60 min) first order rate constant for the reaction was $11.5 \times 10^{-3}$ min$^{-1}$.

Example 11

Hydrocarboxylation of methyl-4-pentenoate using acetonitrile accelerator

A 300 mL glass lined Hastelloy-C shaker tube was charged with toluene (45 mL), methyl-4-pentenoate (4.56 g, 40 mmoles), water (0.72 g, 40 mmoles), acetonitrile (1.64 g, 40 mmoles), methyl iodide (0.57 g), and RhCl$_3$.3H$_2$O (0.11 g, 0.4 mmole).

The tube was closed, cooled to $-78°$ C., evacuated and then pressured with carbon monoxide to 200 psi. The tube was heated with agitation to 130° C. over about 45 min; the total pressure at 160° C. was about 360 psi. The temperature was maintained at 130° C. and additional CO was added at 15 min intervals to maintain the total pressure constant at about 360 psi. The reaction was terminated after 2 h by cooling to 0° C. The excess CO was slowly vented, the product was discharged, and the tube was rinsed twice with two 50 mL portions of methanol.

The product and washings were combined, filtered, and the solution was made up to 200 mL with methanol. The sample was esterified as described in Example 1 and then analyzed as the methyl esters by GC. The analysis showed 51% methyl-4-pentenoate conversion, 16.3% adipic acid, 20.3% 2-methylglutaric acid, 0.93% ethylsuccinic acid, and 2.3% valerolactone. The linearity was 43.4%.

Comparative Example 11A

Hydrocarboxylation of methyl-4-pentenoate in the absence of nitrile accelerators The procedure described in Example 11 was repeated, except that the acetonitrile was omitted. GC analysis of the product showed only 26% methyl-4-pentenoate conversion, 4.6% adipic acid, 2.1% 2-methylglutaric acid, 0.2% ethylsuccinic acid, and 1.7% valerolactone. The linearity was 67%.

Example 12

Hydrocarboxylation of 1-hexene using propionitrile accelerator

The procedure described in Example 11 was repeated, except that the methyl-4-pentenoate was replaced with an equivalent amount of 1-hexene (3.36 g, 40 mmoles) and the acetonitrile was replaced with an equivalent amount of propionitrile (2.2 g, 40 mmoles). GC analysis of the product showed 24.2% recovered hexenes, 1.8% hexane, 44.1% heptanoic acid, 17.3% 2-methylhexanoic acid, and 1.5% 2-ethylpentanoic acid. The linearity was 70.2%.

Comparative Example 12A

Hydrocarboxylation of 1-hexene in the absence of nitrile accelerators

The procedure described in Example 12 was repeated, except that the propionitrile was omitted. GC analysis of the product showed 60.9% recovered hexenes, 1.9% hexane, 22.8% heptanoic acid, 4.4% 2-methylhexanoic acid, and 0.9% 2-ethylpentanoic acid. The linearity was 81.1%.

Example 13

Hydrocarboxylation of 1-hexene using acetonitrile

The procedure described in Example 11 was repeated except that the methyl iodide was replaced with 0.3 g (1.35 meq) of HI as a 57% aqueous solution, the methyl-4-pentenoate was replaced with an equivalent amount of 1-hexene (3.36 g, 40 mmoles), and the temperature was reduced to 120° C. GC analysis of the product showed 38.2% recovered hexenes, 0.1% hexane, 16.8% heptanoic acid, 12.5% 2-methylhexanoic acid, and 1.9% 2-ethylpentanoic acid. The linearity was 53.9%.

Comparative Example 13A

Hydrocarboxylation of 1-hexene in the absence of nitrile accelerators

The procedure described in Example 13 was repeated except that the acetonitrile was omitted. GC analysis of the product showed 52.4% recovered hexenes, 1.3% hexane, 13.0% heptanoic acid, 4.0% 2-methylhexanoic acid, and 1.6% 2-ethylpentanoic acid. The linearity was 69.8%.

I claim:

1. A process for the hydrocarboxylation of a non-conjugated olefinically unsaturated nitrile having the formula:

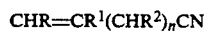

$$CHR = CR^1(CHR^2)_nCN$$

where R and R$^1$ are independently selected from the group consisting of —H, —CH$_3$, —C$_2$H$_5$; R$^2$ is —H, or CH$_3$; and n=1-13 which comprises (a) forming a reaction mixture containing said nitrile, carbon monoxide, water, a rhodium catalyst, a promoter selected from the group consisting of HI, HBr, acetyl bromide, acetyl iodide, alkyl bromides having 1 to 10 carbon atoms and alkyl iodides having 1 to 10 carbon atoms, a solvent selected from the group consisting of methylene chloride, 1,2-dichloroethane, and aromatic solvents having 6 to 9 carbon atoms, in which the concentration of rhodium is in the range of 0.005% to about 0.50% by weight of the reaction mixture, and the molar ratio of nitrile to rhodium is between about 10 and about 700, and the molar ratio of promoter to rhodium is between 1:1 and 20:1, and the amount of solvent is between about 40% and 99% by weight of the reaction mixture, and (b) reacting said mixture at a temperature of 100° C. to about 250° C. and at a carbon monoxide partial pressure in the range of about 200 to about 3,000 psig to form a fixture containing carboxylic acids having one more carbon atom than the non-conjugated olefinically unsaturated nitrile.

2. A process for the hydrocarboxylation of an olefinically unsaturated compound selected from the group consisting of alkenes and non-conjugated olefinically unsaturated esters having the formula:

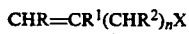

where
- i) X is —C(O)OR$^3$
  R, R$^1$ and R$^3$ are independently selected from the group consisting of —H, —CH$_3$, and —C$_2$H$_5$;
  R$^2$ is —H, —CH$_3$; and
  n=1–5; or
- ii) X is —CH=CH$_2$;
  R and R$^1$ are independently selected from the group consisting of —H, —CH$_3$, and —C$_2$H$_5$;
  R$^2$ is —H or —CH$_3$; and
  n is 0–6; or
- iii) X is —H;
  R and R$^1$ are independently selected from the group consisting of —H, —CH$_3$, and —C$_2$H$_5$;
  R$^2$ is —H or —CH$_3$; and
  n=1–13 which comprises (a) forming a reaction mixture containing said compound, a nitrile accelerator selected from the class consisting of acetonitrile, benzonitrile and propionitrile, carbon monoxide, water, a rhodium catalyst, a promoter selected from the group consisting of HI, HBr, acetyl bromide, acetyl iodide, alkyl bromides having 1 to 10 carbon atoms and alkyl iodides having 1 to 10 carbon atoms, and a solvent selected from the group consisting of methylene chloride, 1,2-dichloroethane, and aromatic solvents having 6 to 9 carbon atoms, in which the concentration of rhodium is in the range of 0.005% to about 0.50% by weight of the reaction mixture and the molar ratio of nitrile to rhodium is between about 10 and about 700, and the molar ratio of promoter to rhodium is between 1:1 and 20:1, and the amount of solvent is between about 40% and 99% by weight of the reaction mixture, and (b) reacting said mixture at a temperature of 100° C. to about 250° C. and at a carbon monoxide partial pressure in the range of about 200 to about 3,000 psig to form a mixture containing carboxylic acids having one more carbon atom than the olefinically unsaturated compound.

3. The process of claim 2 where the olefinically unsaturated compound is selected from the group consisting of methyl-3-pentenoate, methyl-4-pentenoate, 1,3-butadiene, 1,4-pentadiene, 1,5-hexadiene, 1-butene, 1-pentene, 1-hexane, and 1-heptene.

* * * * *